US009029782B2

(12) United States Patent
Maliakal et al.

(10) Patent No.: US 9,029,782 B2
(45) Date of Patent: May 12, 2015

(54) METHOD AND APPARATUS FOR GRAPHENE-BASED CHEMICAL DETECTION

(71) Applicant: LGS Innovations LLC, Herndon, VA (US)

(72) Inventors: Ashok J. Maliakal, Westfield, NJ (US); Brijesh Vyas, Warren, NJ (US); Hugo Safar, Westfield, NJ (US)

(73) Assignee: LGS Innovations LLC, Herndon, VA (US)

( * ) Notice: Subject to any disclaimer, the term of this patent is extended or adjusted under 35 U.S.C. 154(b) by 211 days.

(21) Appl. No.: 13/653,630

(22) Filed: Oct. 17, 2012

(65) Prior Publication Data

US 2014/0103213 A1    Apr. 17, 2014

(51) Int. Cl.
*G01J 5/02* (2006.01)
*G02B 6/10* (2006.01)
*G02B 6/12* (2006.01)

(52) U.S. Cl.
CPC ........ *G02B 6/10* (2013.01); *G02B 2006/12035* (2013.01)

(58) Field of Classification Search
CPC ............... G02B 6/122; G01N 21/7703; G01N 21/7706; G01N 21/7716; G01N 202/7783; G01N 202/7709
USPC ..................... 385/123, 12, 30, 124, 126, 128; 250/343, 338.1, 227.14, 227.11, 250/227.21; 356/436
See application file for complete search history.

(56) References Cited

U.S. PATENT DOCUMENTS

| | | | | |
|---|---|---|---|---|
| 5,684,907 | A * | 11/1997 | Sprehn et al. | 385/123 |
| 2011/0091150 | A1 * | 4/2011 | Caron et al. | 385/12 |
| 2011/0158268 | A1 * | 6/2011 | Song | 372/18 |
| 2012/0161106 | A1 * | 6/2012 | Kim et al. | 257/29 |

OTHER PUBLICATIONS

Yavari et al., "Graphene Based Chemical Sensors," The Journal of Physical Chemistry Letters, vol. 3, pp. 1746-153; published Jun. 14, 2012; Retrieved from internet [Sep. 2, 2014]; Retrieved from URL <http://pubs.acs.org/doi/pdf/10.1021/5z300358t>.*
Liu, et al., "A graphene-based broadband optical modulator," Letter, Nature, vol. 474, pp. 64-67; published Jun. 2011; Retrieved from internet [Sep. 3, 2014]; Retrieved from URL <http:www.nature.com/nature/journal/v474/n7349/full/nature10067.html>.*
Schnitzer, et al., "Fiber-optic-based evanescent field chemical sensor using tunable diode lasers for the mid-infrared spectral region," Journal of Applied Physics, vol. 66, p. 5667; published 1989; Retrieved from Internet [Sep. 3, 2014]; Retrieved from URL <http://dx.doi.org/10.1063/1.343635>.*

* cited by examiner

*Primary Examiner* — Yara B Green
(74) *Attorney, Agent, or Firm* — Baker & Hostetler LLP

(57) ABSTRACT

A chemical sensor is provided. The sensor includes at least one lightguiding element having an optical core. The lightguiding element comprises a layer of graphene situated in sufficient proximity to the core to exhibit evanescent wave absorption of optical energy in at least one optical mode guided in the core.

13 Claims, 4 Drawing Sheets

METHOD AND APPARATUS FOR GRAPHENE-BASED CHEMICAL DETECTION

FIELD OF THE INVENTION

The invention relates to sensors for chemical detection, and more particularly to sensors that exhibit detectable changes in their physical properties in the presence of surface-bound analytes.

ART BACKGROUND

There is considerable interest in methods for detecting airborne and waterborne chemical contaminants, among others, that are present in small concentrations in a carrier fluid. In one class of sensors useful for such purposes, selective binding events take place between the analyte and receptor molecules in the sensor, resulting in a measurable change in the physical properties of the receptor. For example, in a method for detecting airborne molecules of explosive compounds such as the nitroaromatics 2,4,6-trinitrotoluene (TNT) and hexahydro-1,3,5-trinitro-1,3,5-triazine (RDX) as well as other nitro compounds such as pentaerythritol tetranitrate (PETN), binding of the analyte molecules to fluorescent polymers causes detectable fluorescence quenching.

Despite this and other similar technologies, however, there remains a need for improved chemical sensors with greater sensitivity, selectivity, and reliability. In particular, there is a need for an integrated chemical sensor which combines excellent sensitivity and selectivity with a small form factor that ideally could be integrated into portable devices such as smart phones.

SUMMARY OF THE INVENTION

Such a sensor will be described here. The sensor uses graphene as a sensitive medium for detecting explosive nitroaromatics and other chemical compounds. By "graphene" is meant graphene having electronic or optical properties indicative of a graphene composition that, in relation to the purpose for which it is to be used, is effectively of monolayer or bilayer structure. Although monolayer graphene will be generally be assumed in the examples provided below, we believe that similar devices based on graphene structures having several layers can also be made and usefully employed, and should not be excluded as possible embodiments of our invention.

Graphene is known to form charge-transfer complexes with a number of compounds, notably including many nitroaromatic compounds. The charge transfer phenomenon leads to doping of the underlying graphene layer with charge carriers.

Nitroaromatics, for example, are strong electron acceptors, and as a consequence they tend to dope the underlying graphene with holes. As will be explained in greater detail below, this doping effect can be detected through optical absorption modulation.

Accordingly, the invention in one embodiment includes at least one lightguiding element having an optical core. The lightguiding element comprises a layer of graphene situated in sufficient proximity to the core to exhibit evanescent wave absorption of optical energy in at least one optical mode guided in the core.

DETAILED DESCRIPTION

Monolayer graphene has recently become available from commercial sources, and can also be made in a suitably equipped laboratory according to any of various published methods. It is a two-dimensional material such that every atom in the monolayer structure is part of the surface and available for interaction in sensing. Electronically, monolayer graphene is a zero-overlap semimetal with a linear dispersion relation for charge carriers around the Dirac point. This property permits precise control of the charge carrier density within the graphene layer by means of an applied gate voltage. By virtue of the same property, the charge carrier density is very sensitive to chemical doping.

Moreover, the binding of an analyte to a graphene domain will dope the entire domain. The sensor utilizes this property by disposing the graphene layer over the surface of an optical waveguide in such a way that the evanescent portion of the guided optical mode penetrates into the graphene layer and suffers a degree of extinction that is sensitive to the doping of the graphene layer.

Even if the graphene sheet has only a small area interacting with the analyte, the entire area of the graphene domain will be doped in consequence of contact with the analyte, and the entire area will be interrogated by the evanescent wave due to the guided mode. The waveguide can be fabricated with a relatively long pathlength, for example by fabricating it in a serpentine configuration, to provide enhanced sensitivity as a consequence of multiple absorption events.

As noted, chemical species that may be detected in this manner include various nitroaromatic compounds. Other candidate species for detection in this manner are organophosphorus nerve agents and DNA. For detection of some species, such as those susceptible to phosphonate (organic phosphorus) bonding to the graphene layer, it may be desirable to sensitize the graphene by funtionalizing it with oxygen functionality.

Figure 1:
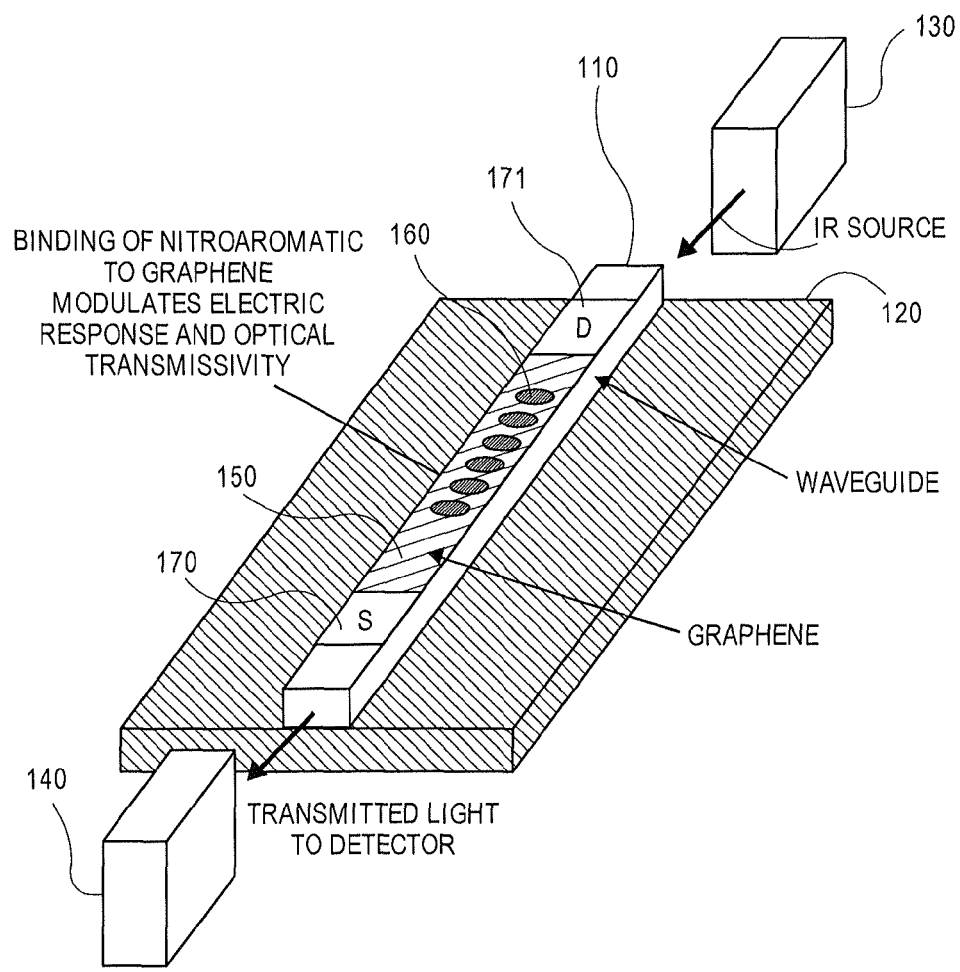
FIG. 1 is a semischematic perspective view of an infrared waveguide adapted for use as a chemical sensor.

FIG. 1 is a semischematic perspective view of an infrared waveguide adapted for use as a chemical sensor. With reference to the figure, waveguide 110 is formed on substrate 120 and optically coupled at one end to infrared source 130 and at the other end to infrared detector 140. Graphene layer 150 is deposited on the upper face, i.e., the face distal substrate 120, of the waveguide. As noted above, layer 150 is exemplarily monolayer graphene but could alternatively be a graphene structure having several layers.

Waveguide 110 can be made of any suitable material that is optically transmissive near an optical absorption edge of graphene, for example in the range 1.0-1.5 micrometers, although different optical windows may also be appropriate for different applications. Both silicon and silica may be suitable in this regard. Similarly, substrate 120 can be made from silicon, silica, or any other suitable material.

As will be seen below, it can in some cases be advantageous to use silicon for the substrate material so that the substrate can also serve as a gate electrode. As will also be seen below, a waveguide formed on a silicon substrate is advantageously made from silica or another dielectric material to provide electrical isolation between the substrate and the graphene layer that overlies the waveguide.

In some embodiments, a pair of electrodes 170, 171 are formed as metal layers such as gold or chromium deposited by, e.g., sputtering or evaporation, in electrical contact with opposite ends of the graphene layer. Electrodes 170, 171 are connected to a source of electric current (not shown) to be used for ohmic heating of the graphene layer. The heating circuit also establishes the reference voltage relative to which a potential applied to the silicon substrate or other gate electrode will induce changes in the electrical carrier density within the graphene layer.

Spots 160 in the figure represent portions of the graphene layer which have bonded to analyte molecules. The analyte, as mentioned above, will typically be present in ambient air, or in a body of water to be tested, or in another gaseous or liquid carrier fluid. Contact between the graphene layer and the carrier fluid may be initiated, e.g., by opening an inlet and activating a fan, pump, or other impeller so that the carrier fluid passes through the inlet into a chamber containing the sensor structure. It is well known that the typical structure of a planar waveguide such as waveguide 110 includes a core layer of higher refractive index, enclosed between upper and lower cladding layers of lower refractive index. However, at least part of the cladding function can be provided in some cases directly by the substrate, or by air or another low-index material surrounding the core. To simplify the presentation, no cladding has been explicitly shown in FIG. 1 or any of the other figures. However, it should be understood that if desired, a lower cladding layer is readily added between the waveguide core and the substrate, and an upper cladding layer is readily added over the upper face of the core layer.

However, the evanescent portion of the electromagnetic field guided as an optical mode (or combination of optical modes) in the core layer must reach close enough to the graphene layer, or far enough into the graphene layer, to be affected by it. For this to occur, the graphene layer should be placed within close proximity to the upper face of the core layer (typically less than roughly 100-150 nm, and preferably less than about 50 nm). If there is an upper cladding layer, a portion of it can be removed to create a window within which the graphene layer is emplaced.

As noted above, a potential applied to a gate electrode can be used to induce changes in the graphene carrier density. More specifically, the gate voltage can be used to tune the Fermi level of the graphene layer.

For example, Liu, M. et al., "A graphene-based broadband optical modulator," *Nature* 2011, 474, 64-67 reported on the transmissive properties of a silicon waveguide overlain by monolayer graphene at an infrared wavelength of 1.53 micrometers while subjected to a gate voltage. At gate voltages in the range −1V to 3.8V, interband transitions were able to occur, resulting in optical absorption in the graphene, which through evanescent absorption led to a decrease in the transmissivity of the waveguide. However, at gate voltages below −1V, the graphene became transparent due to the absence of filled electron states in the valence band at the appropriate energies available for interband infrared transitions. Likewise, at gate voltages above 3.8V, the graphene again became transparent at these wavelengths because of filling of conduction-band states.

In our invention, the carrier density in the graphene layer is modified by the attachment of analyte molecules to the graphene film. In turn, changes in charge density in the graphene change its optical properties that modify the transmissivity of the waveguide.

We also incorporate in our sensor a gate voltage control, to electrically modify the graphene's properties for maximum molecular detection sensitivity, e.g., to bias the device into a regime where the graphene is opaque, but where exposure to analyte molecules will cause the greatest increase in transparency. Based on the Liu et al. *Nature* 2011 article cited above, for example, we believe that the gate voltage could be set to somewhat above −1V, so that attachment of electron-acceptor analyte molecules would cause the graphene to switch from an opaque to a transparent state, resulting in increased transmissivity of the waveguide.

Furthermore, to provide our sensor with chemical selectivity, a thin aerogel film is deposited over the graphene layer of at least one sensor, whereas at least one other sensor has no corresponding aerogel film or has an overlying aerogel film of less thickness. Aerogels, also referred to as organically modified porous silica, are mesoporous silicas that can be formulated as thin films. Because they are mesoporous, they permit diffusion of small molecules and gases on readily observable timescales. For our sensor, a typical thickness for the aerogel film will be in the range of one to several hundred nanometers. Diffusion times of analytes through such a film will typically be on the order of seconds.

It should be noted in this regard that alternatives to aerogels, which may be more useful when the carrier fluid is a liquid, include hydrogels. A hydrogel is a polymer that interacts with water to form a porous network.

The diffusion of the analyte through the, e.g., aerogel film has a temporal profile that can be measured from changes, over time, in the transmissivity of the waveguide. By comparing the response of the bare sensor to the response of the aerogel-covered sensor, or by comparing the responses of sensors having different aerogel thicknesses, it is possible to obtain at least a relative value of the diffusivity of the analyte in the aerogel. This measured diffusivity will be characteristic for different chemical agents, and will be used to identify different analytes.

Figure 2:
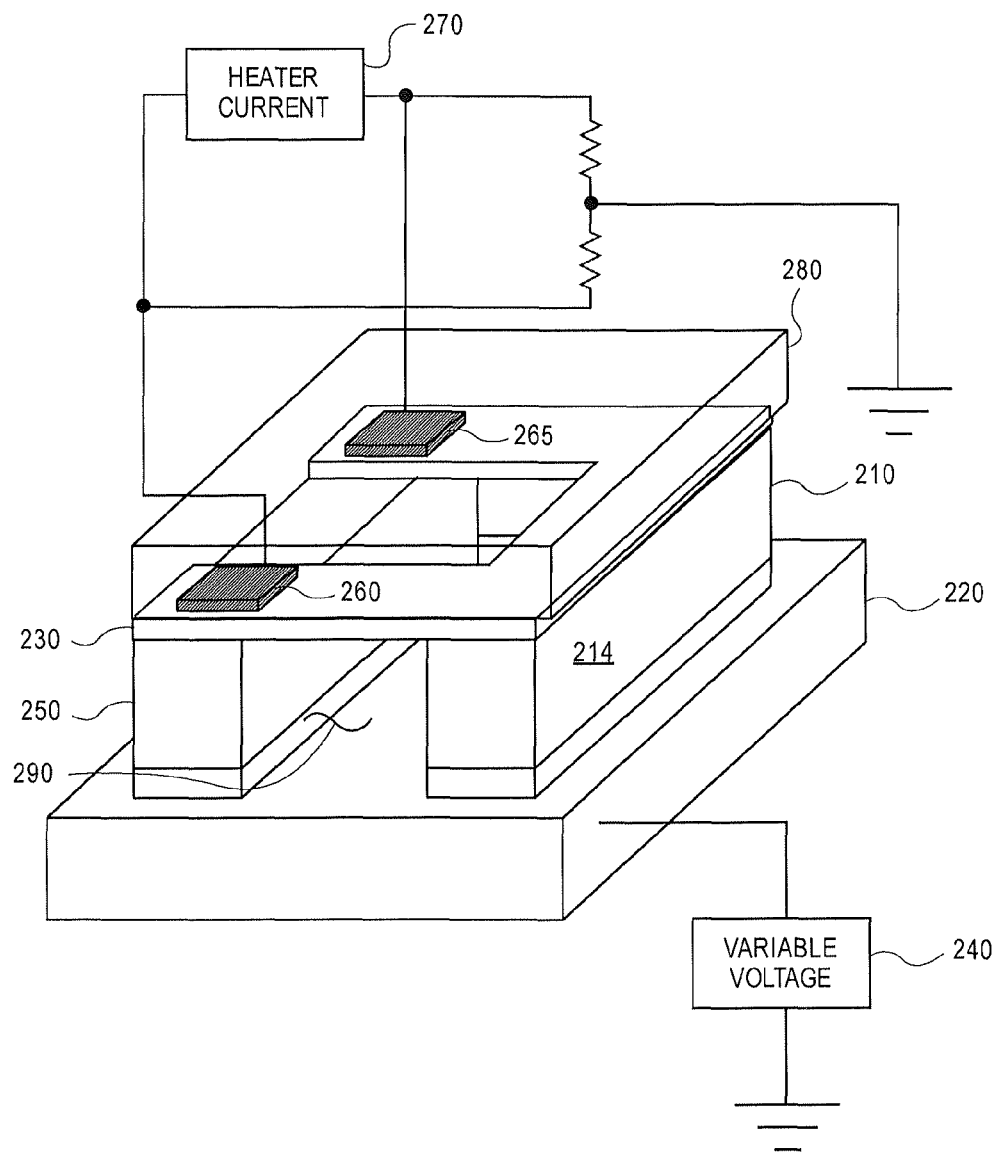
FIG. 2 is a partially schematic perspective drawing, not to scale, of one example of an aerogel-coated sensor having a design that can be fabricated using well-known techniques.

FIG. 2 is a partially schematic perspective drawing, not to scale, of one example of an aerogel-coated sensor having a design that can be fabricated using well-known techniques. As seen in the figure, waveguide 210 is a silica waveguide formed on silicon substrate 220. Waveguide 210 has a lower cladding portion 212 of undoped silica, and a core portion 214 of silica that has been doped with, e.g., phosphorus to increase its refractive index according to known principles. The waveguide will typically be several centimeters in length.

The light source and detector, which are not shown in FIG. 2, are advantageously fabricated and coupled to the waveguide using known techniques of on-chip integration. In particular, a fixed-wavelength or tuneable laser source and a photodiode detector can be emplaced on a planar lightwave component (PLC) chip using well-known flip-chip techniques.

As seen in the figure, waveguide 210 has no upper cladding layer. However, an upper cladding layer of, e.g., undoped silica may optionally be added, providing that the upper cladding is thin enough for the evanescent field to penetrate through it and into the overlying graphene layer 230, or alternatively, that a window is defined in the upper cladding to permit direct contact between the graphene layer and core 214.

Substrate 220 is advantageously made conductive by doping it with, e.g., an n-type dopant so that it can function as the gate electrode. As seen in the figure, the gate voltage is provided by variable voltage source 240.

A silica support member 250 is formed on the substrate in parallel with waveguide 210. Graphene layer 230 is partially supported by waveguide 210, and partially supported by support member 250. In one possible method for forming layer 230, monolayer graphene is deposited by transfer from commercially available monolayer CVD (chemical vapor deposition) films. In alternative approaches, the graphene layer is produced by mechanical exfoliation or from thermal conversion of patterned polymer films with nickel catalysis.

Heater electrode contacts 260, 265 are formed by, e.g., depositing electron-beam evaporated gold on the respective portions of the graphene layer that overlie support member 250. As seen in the figure, the heater contacts are electrically connected to low-voltage current source 270, which provides current for ohmic heating of the graphene layer. Prior to using the sensor, it is advantageous to heat the graphene to drive off impurities that have attached to the graphene surface, so that the graphene is effectively undoped upon initial exposure to the reactant that is to be detected.

The heating circuit can also be used for chemical analysis by temperature-programmed desorption. That is, the temperature of the heated graphene can be gradually increased while monitoring the transmissivity of the waveguide. At characteristic desorption temperatures, various chemical species will become volatile and will detach from the graphene layer, causing changes in the transmissivity of the waveguide. By identifying the desorption temperatures, it is possible to at least partially identify the chemical species.

The simple resistor network shown in the figure is meant to symbolically indicate that through the heater contacts, the graphene film is maintained substantially at ground potential.

Turning back to FIG. 2, it will be seen that the graphene film is overlain by aerogel layer 280. As noted above, reactants can be at least partially identified by their diffusion profiles through the aerogel layer.

It should also be noted that at least some reactants can be excluded from the aerogel layer, and thus prevented from reaching the graphene, if the aerogel has been appropriately functionalized. Accordingly, greater selectivity can be achieved by providing an array of aerogel-covered sensors, in which each aerogel has been functionalized to exclude a respective chemical species or group of chemical species.

As seen in the figure, there is an empty space 290 between waveguide 210 and support member 250. In some implementations, space 290 may simply be air-filled, or it may be filled with, e.g., a foam, a low-refractive-index polymer, or another material of lower refractive index than core 214. Likewise, the outward-facing (as seen in the figure) lateral walls of the waveguide and support member may be bounded by air or by another low-index material.

Figure 3:
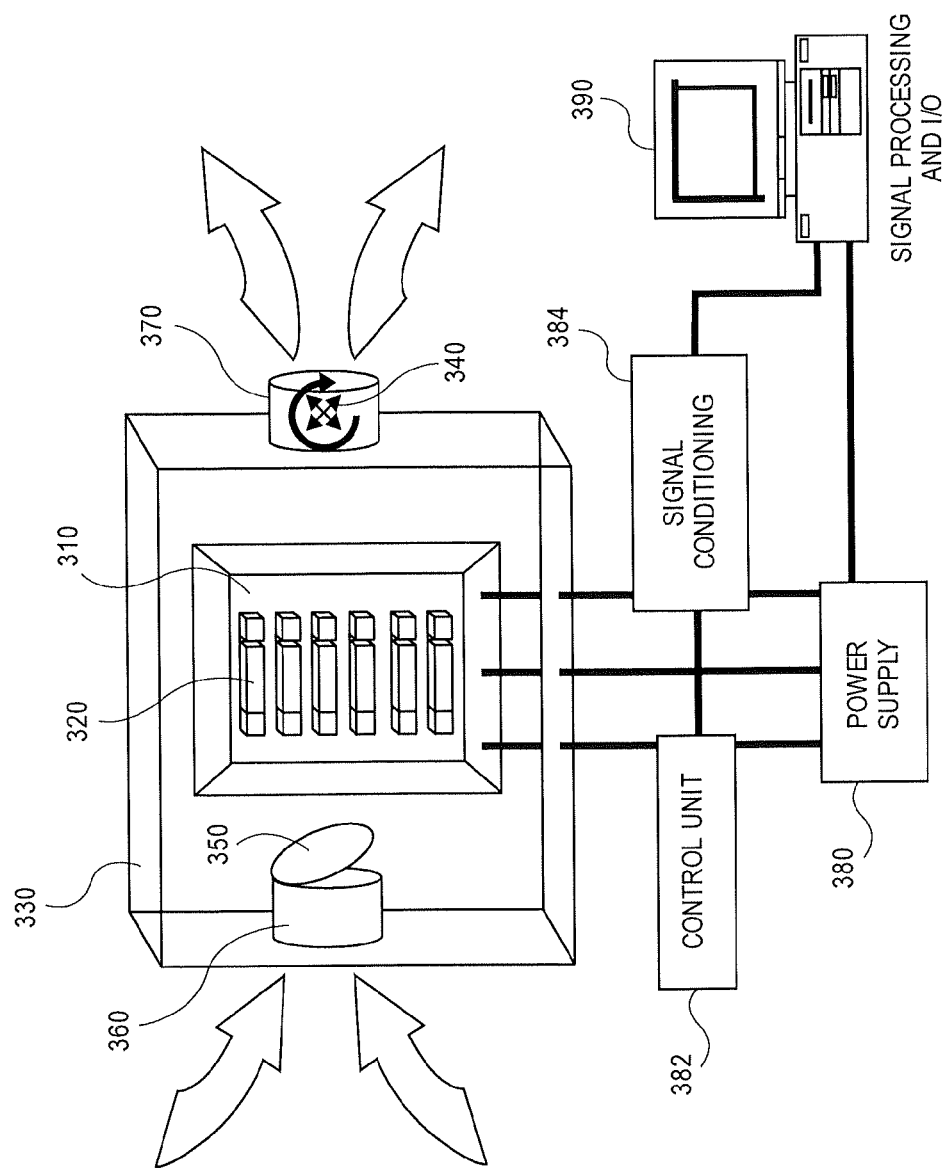
FIG. 3 provides a schematic representation of an exemplary system in which an array of multiple sensors of, e.g., the type represented in FIG. 2 are mounted within an enclosure.

FIG. 3 provides a schematic representation of an exemplary system in which an array 310 of multiple sensors 320 of, e.g., the type represented in FIG. 2 are mounted within an enclosure 330. The enclosure is normally airtight, but upon actuation of fan or other impeller 340 and opening of appropriate valves or shutters such as shutter 350, ambient air is admitted through inlet 360. The admitted air comes into contact with the sensors of array 310 before exiting the enclosure through outlet 370. It will be understood that a similar arrangement can be used for analysis of other fluids, such as water.

Each sensor of array 310 includes a light source, a waveguide, and an optical detector as described above. In alternate implementations, optical output from a single light source may be split and distributed by optical fibers or other appropriate light-guiding components to each of the respective waveguides. Power to the sources and detectors, and for heating the graphene layers, is provided by power supply 380. Control for the sources and detectors, for the heating circuit, and for the gate voltages applied to the respective sensors is provided by control unit 382. The signal output from the detectors is conditioned by signal conditioning unit 384 and directed, exemplarily on a suitable data bus, to device 390 for signal processing and output from, e.g., a display screen. Device 390 may include a keyboard or other input device for inputting data and control commands. In some implementations, device 390 may be a smartphone operative under the control of suitable application software to perform data processing and input/output operations.

When the sensors are operated using fixed-wavelength light sources, it will be advantageous, as noted above, to tune the gate voltages to optimize the response, i.e., to provide a relatively large change in waveguide transmissivity in response to the presence of analyte molecules. When wavelength-tuneable light sources are used, the response may be optimized in either the wavelength domain, or the gate-voltage domain, or jointly in both domains.

In one possible mode of operation, the detector output is monitored while sweeping the output from a tuneable light source over a range of wavelengths to obtain a spectrum. The gate voltage would typically be held constant in such an operation. In another possible mode of operation, the detector output is monitored at fixed wavelength from the optical source, while the gate voltage is swept over a range of values. In yet another possible mode of operation, the spectral information is obtained, as described above, over a range of gate voltages.

In the foregoing discussion, the optical sensing based on optically absorptive transitions between the conduction band and the valence band of monolayer graphene is described. It should be noted in this regard that other optical processes may also contribute to changes in the transmissivity of the waveguide and hence may also be utilized by the sensors. For example, bilayer graphene and graphene having one or a few further layers also exhibit optical absorption changes due to chemical doping, and as a consequence optical sensing may be based on materials such as these. It should be noted, however, that the effect tends to become more attenuated as the number of layers of carbon increases, and at ten or more layers, behavior sufficiently observable to be useful in a chemical sensor is unlikely.

In the foregoing discussion, one example of an optical sensor using a silica waveguide, i.e., waveguide 210 of FIG. 2, has been provided. It should be stressed that such an example is merely illustrative, and not to be considered as limiting. Thus, for example, it may prove advantageous in at least some cases to provide a sensor in which the light-guiding medium is silicon. An example of such a sensor structure, in a configuration that lends itself well to known fabrication techniques, is provided in FIG. 4.

Figure 4:
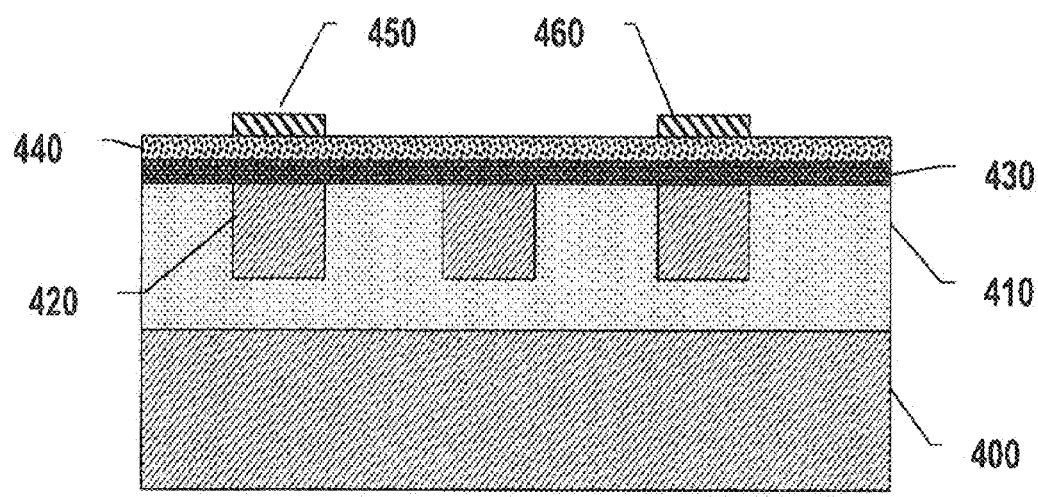
FIG. 4 is a partially schematic perspective drawing, not to scale, of a second example of an aerogel-coated sensor having a design that can be fabricated using well-known techniques.

With reference to FIG. 4, there is provided a silicon substrate 400, on which is formed a silica layer 410 which provides electrical isolation and also forms a cladding for silicon waveguide structure 420 which is formed adjacent to layer 410. As seen in the figure, layer 410 is formed so as to both underlie waveguide 420 and laterally adjoin the waveguide structure. Alternatively, layer 410 may comprise two layers: FINOne layer that underlies the waveguide structure and a second layer that laterally envelopes the waveguide structure.

The exemplary waveguide shown in the figure has a serpentine configuration, seen as an end-on view of three lobes in the cross-sectional view of the figure. Waveguide 420 is advantageously made conductive by n-type doping, so that it can also serve as the gate electrode.

A gate oxide layer 430, exemplarily composed of aluminum oxide, is deposited on the upper surface of waveguide

420. Layer 430 provides electrical isolation between the waveguide and graphene layer 440, which is formed on layer 430. Reference and heating electrodes 450, 460 are formed on the graphene layer, exemplarily by vapor deposition of gold.

We claim:

1. Apparatus comprising:
    at least one lightguiding element having an optical core; wherein
    the lightguiding element comprises a layer of graphene situated in sufficient proximity to the core to exhibit evanescent wave absorption of optical energy in at least one optical mode guided in the core,
    the lightguiding element is one of two or more lightguiding elements, each having a core and a graphene layer in proximity to the core,
    each lightguiding element is optically coupled to an optical source arranged to inject light into said element and an optical detector arranged to measure optical loss by detecting light coupled out of said element,
    one or more diffusion layers of aerogel overlay the graphene layers of one or more respective lightguiding elements, and
    at least one lightguiding element has no diffusion layer or at least two lightguiding elements have diffusion layers of different thicknesses.

2. The apparatus of claim 1, wherein the lightguiding element has a principal direction of optical propagation, and the graphene layer is elongated in said principal direction.

3. The apparatus of claim 2, further comprising an optical source and an optical detector optically coupled to the lightguiding element, wherein the source is arranged to inject light into said element and the detector is arranged to measure optical loss by detecting light coupled out of said element.

4. The apparatus of claim 3, wherein the optical source is a tuneable laser.

5. The apparatus of claim 3, wherein the lightguiding element comprises at least a portion of a planar lightwave circuit in which a cladding layer overlies the core, and wherein the graphene layer is included within the cladding layer.

6. The apparatus of claim 1, further comprising a circuit configured to compare at least two lightguiding elements by measuring a delay between changes in the optical loss that occur in the respective elements when the apparatus is activated by a chemical agent.

7. The apparatus of claim 6, wherein each graphene layer is electrically isolated from a respective gate electrode and the apparatus further comprises a voltage source arranged to apply an adjustable electrical voltage between each graphene layer and its respective gate electrode.

8. The apparatus of claim 7, wherein two or more of the graphene layers are overlain by respective aerogel layers, each aerogel layer is chemically functionalized to suppress the diffusion therethrough of one or more selected chemical species, and at least two of the aerogel layers are functionalized in respect to different selections of chemical species.

9. The apparatus of claim 1, wherein the graphene layer is electrically isolated from a gate electrode and the apparatus further comprises a voltage source arranged to apply an adjustable electrical voltage between the graphene layer and the gate electrode.

10. The apparatus of claim 1, further comprising an electric current source and a pair of electrical contacts arranged for passing the electric current through the graphene layer.

11. A system comprising:
    a sealable enclosure having at least one fluid inlet and at least one fluid outlet;
    one or more sensors contained within the sealable enclosure, wherein each of the sensors comprises a lightguiding element having an optical core and a layer of graphene situated in sufficient proximity to the core to exhibit evanescent wave absorption of optical energy in at least one optical mode guided in the core, and each of the sensors is optically coupled to an optical source and an optical detector;
    an impeller for moving fluid through the enclosure;
    a circuit adapted to apply a controllable gate voltage between the graphene layer of each sensor and a gate electrode;
    a circuit adapted to activate at least one said optical source;
    a circuit adapted to activate at least one said optical detector;
    a circuit adapted to receive signals from at least one said detector and to provide output derived from the detector signals; and
    a current source adapted to drive an ohmic heating current through at least one said graphene layer and a control circuit adapted to scan the current over a range of values.

12. The system of claim 11, wherein at least one of the optical sources is a tuneable laser and the optical source-activating circuit is adapted to scan optical output from the laser over a range of wavelengths.

13. The system of claim 11, wherein the gate-voltage-applying circuit is adapted to scan the gate voltage over a range of values.

* * * * *